United States Patent [19]

Maurer et al.

[11] 4,008,184
[45] Feb. 15, 1977

[54] 6,10 DIMETHYL BICYCLO(4,4,0)DECANE OR DECENE ALCOHOL AND ESTER PERFUME COMPOSITIONS

[75] Inventors: Bruno Maurer, Collonge-Bellerive; Michel G. Fracheboud; Günther Ohloff, both of Bernex-Geneva, all of Switzerland

[73] Assignee: Firmenich S.A., Geneva, Switzerland

[22] Filed: Feb. 20, 1976

[21] Appl. No.: 659,897

Related U.S. Application Data

[62] Division of Ser. No. 363,192, May 23, 1973, abandoned.

[30] Foreign Application Priority Data

June 29, 1972   Luxembourg .......................... 65499

[52] U.S. Cl. ............................ 252/522; 260/488 B; 260/617 F
[51] Int. Cl.$^2$ .......................................... C11B 9/10
[58] Field of Search ............ 252/522, 488 B, 617 F

[56] References Cited

UNITED STATES PATENTS

| | | | |
|---|---|---|---|
| 2,802,880 | 8/1957 | Stoll et al. ...................... | 260/617 F |
| 3,819,711 | 6/1974 | Bozzato et al. .................... | 252/522 |
| 3,870,659 | 3/1975 | Bozzato et al. .................... | 252/522 |
| 3,929,894 | 12/1975 | Leitereg et al. .................... | 252/522 |

OTHER PUBLICATIONS

Chem. Ab., 63:14916e, 1965.
Chem. Ab., 64:1578e, 1966.

*Primary Examiner*—Veronica O'Keefe
*Attorney, Agent, or Firm*—Pennie & Edmonds

[57] ABSTRACT

Use of bicyclic compounds, some of which are new, as perfuming and/or flavoring ingredients in the manufacture of perfumes and perfumed products and/or in the preparation of artificial flavors for foodstuffs, animal feeds, beverages, pharmaceutical preparations and tobacco products.

Process for the preparation of said bicyclic compounds.

7 Claims, No Drawings

6,10 DIMETHYL BICYCLO(4,4,0)DECANE OR DECENE ALCOHOL AND ESTER PERFUME COMPOSITIONS

This is division, of application serial no. 363,192 filed May 23, 1973 now abandoned.

SUMMARY OF THE INVENTION

The invention relates to the use of a new class of valuable perfuming and/or flavouring ingredients. Said ingredients are bicyclic compounds of formula

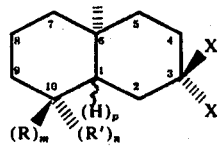

I containing a single or a double bond in one of the positions indicated by the dotted lines and wherein the indexes m, n and p represent the integers zero or 1, the symbols X when taken together represent an oxygen atom, or when taken separately one of them represents a hydroxyl or an O-acyl group and the other represents a hydrogen atom, and wherein
  i. the symbol R represents a lower alkyl group when both n and p are identical and equal to zero and m is 1; or
  ii. one of the symbols R and R' represents a lower alkyl group and the other is a hydrogen atom when both m and n are identical and equal to 1 and p is zero; or
  iii. one of the symbols R and R' represents a lower alkyl group and the other is a hydrogen atom when all indexes m, n and p are equal to 1.

The invention also relates to new bicyclic compounds of formula

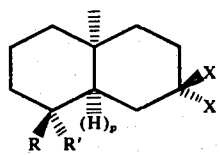

Ia containing a single or a double bond in the position indicated by the dotted line, wherein the index p is zero or 1, the symbol R' represents a lower alkyl group and R is a hydrogen atom and wherein the symbols X are defined as in formula I; or of formula

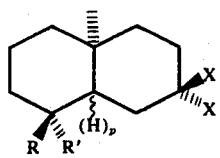

Ib containing a single or a double bond in the position indicated by the dotted line, wherein the index p is zero or 1, the symbol R represents a lower alkyl group and R' is hydrogen and wherein one of the symbols X represents a hydroxyl or an O-acyl group and the other is a hydrogen atom; or of formula

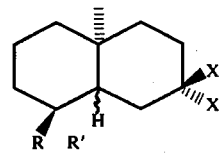

Ic wherein the symbol R represents a lower alkyl group and wherein the symbols X when taken together represent an oxygen atom, or when taken separately one of them represents an O-acyl group and the other is a hydrogen atom; or of formula

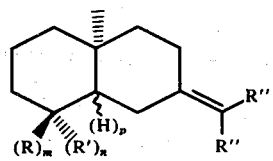

Id wherein the two symbols X are taken together and represent an oxygen atom, the symbol R represents a lower alkyl group and R' is a hydrogen atom.

The invention further relates to a process for the preparation of bicyclic compounds of formula I which comprises:

A. oxidizing a compound of formula

II wherein each of the symbols R'' represents a lower alkyl group, and wherein the position of the possible double bond, the symbols R and R' and the indexes m, n and p have the same meaning as for formula I, by means of singlet oxygen and treating the thus obtained oxidation mixture with an acidic reagent to afford a compound of formula I wherein the symbols X are taken together and represent an oxygen atom; or B. oxidizing a compound of formula II as set forth under letter A by means of an oxidizing agent able to split the exocyclic double bond of compound II to afford a compound of formula I as set forth under letter A; or C. reducing the ketone obtained under letter A or B to afford a compound of formula I wherein one of the symbols X represents a hydroxyl group and the other is a hydrogen atom and wherein the symbols R and R' and the indexes m, n and p are defined as indicated under letter A or B; or D. esterifying the alcohol obtained under letter C to afford a compound of formula I wherein one of the symbols X represents an O-acyl group and the other is a hydrogen atom and wherein the symbols R and R' and the indexes m, n and p are defined as indicated under letter C; or E. isomerizing the cyclic double bond of a compound of formula I, wherein the symbols are taken together and represent an oxygen atom and wherein the symbols R and R' and the indexes m, n and p are defined as indicated under ii), — to afford a compound of formula I wherein the symbols X have the same meaning as hereinabove and wherein the symbols R and R' and the indexes m, n and p are defined as indicated under i); or F. reducing the ketone obtained under letter E to afford a compound of formula I wherein one of the symbols X represents a hydroxyl group and the other is a hydrogen atom and wherein the symbols R and R' and the indexes m, n and p are defined as indicated under letter E; or G. esterifying the alcohol obtained under letter F to afford a compound of formula I wherein one of the symbols X represents an O-acyl group and the other is a hydrogen atom and wherein the symbols R and R' and the indexes m, n and p are defined as indicated under letter F.

BACKGROUND OF THE INVENTION

Among the new compounds which can be prepared by the process of the invention, (+) trans-6,10-dimethyl-bicyclo[4.4.0]dec-1-en-3-one is a naturally occurring compound. The said ketone was in fact isolated for the first time from vetiver Reunion oil (Vetiveria zizanioides), by means of an extremely complex and expensive process. The said isolation process first consisted in separating the ketonic fraction of the natural essential oil by treating this letter with the Girard's reagent [see Helv. Chim. Acta 22, 640 (1939)]. After hydrolysis the recovered pure ketonic fraction was the submitted to several fractional distillations, a new ketonic fraction containing a high proportion of the desired compound was thus obtained. Pure (+) trans-6,10-dimethyl-bicyclo[4.4.0]dec-1-en-3-one was finally obtained by preparative vapour phase chromatography. It has to be pointed out that said ketone is a very minor constituent of natural vetiver oil, this latter containing in fact a proportion from about 0.1–0.2% (parts by weight) of said compound.

The pure ketone possesses a very distinct and powerful odour presenting an original woody character. Moreover, this odour is very stable and easily reproducible whereas the odour of the natural essential oil, which results from the overlapping of the odour of each individual constituent of the said oil, can vary depending on the origin and the purity of the said natural essential oil.

Owing to its particular olfactive properties the above mentioned bicyclic ketone can be widely used in the art of perfumery. Its use is broader than that of vetiver oil itself and it enables the perfumer to create totally original woody notes. Furthermore, the said ketone possesses a very appreciated reinforcing and fixative effect.

Hitherto, (+) trans-6,10-dimethyl-bicyclo[4.4.0]dec-1-en-3-one represents the first known example of a compound having a ketonic structure with a skeleton containing 12 carbon atoms found in vetiver oil. The said discovery has thus encouraged the man in the art to further explore a whole series of analogous bicyclic derivatives which represent a new class of valuable perfuming ingredients.

The above ketone can also be obtained by a process consisting in the separation of the two enantiomeric constituents of the known racemic compound, e.g. via the corresponding semi-carbazone derivative [see J. Am. Chem. Soc. 80, 6551 (1958)]. The said process can also be effected by separating the corresponding racemic unsaturated alcohol via the ester prepared from α-bromo-camphor sulfonic acid the said bicyclic alcohol [see J. Am. Chem. Soc. 91, 535 (1969)], and followed by a regeneration and subsequent oxidation of the thus obtained optically active alcohol.

By means of a novel process of synthesis industrially and economically more advantageous than the isolation of the said ketone from the natural vetiver oil, it is now possible to put to the disposal of perfumers and flavourists a practically pure trans-6,10-dimethyl-bicyclo[4.4.0]dec-1-en-3-one. The difficulties of supply, storage and purification of the natural essential oil are thus avoided.

PREFERRED EMBODIMENTS OF THE INVENTION

In the definition of the above mentioned formulae the term "lower alkyl group" is here defined to mean a branched or linear alkyl group containing from 1 to 6 carbon atoms, as e.g. a methyl, ethyl, n-propyl, isopropyl, n-butyl, isobutyl or ter-butyl group.

The compounds of formula I wherein one of the symbols R and R' represents a methyl grup and the other is a hydrogen atom possess a sesquiterpenoid skeleton containing 12 carbon atoms. Hitherto, the use of these specific compounds as perfuming and/or flavouring ingredients had never been recognized in the art.

We have now found that compounds of formula I possess interesting organoleptic properties and represent very useful ingredients for the preparation of perfumes or perfumed products as well as for the reconstruction of essential oils. We have equally found that the said compounds are particularly appreciated in the preparation of various artificial flavours and for flavouring foodstuffs, animals feeds, beverages, pharmaceutical preparations and tobacco products.

In the perfumery the compounds of formula I can improve, enhance or modify various olfactive notes, e.g. woody earthy or balsamic notes. By the use of the compounds of formula I, it is thus possible to create perfume compositions possessing a modern or more classical new fresh and woody character reminiscent in some instances of the odour of amber, ylang, sandelwood or patchouli for example. It was furthermore noticed that the thus improved or modified woody notes were, in some cases, particularly tenacious. The use of the said compounds is also appreciated for the manufacture of perfumed products as e.g. soaps, detergents, waxes, cleaning products or cosmetic preparations.

When the compounds of formula I are used as perfuming ingredients in perfume compositions the more interesting effects are achieved by the use of proportions comprised between about 0.5 and about 2% of the total weight of the perfumed composition. Depending on the desired effect or on the nature of the other constituents of a given composition, lower, e.g. of the order of 0.01%, or higher concentrations, from about 5 to 10% (parts by weight), can also be used. When the said compounds are used as reinforcing ingredients in perfumed bases the used concentrations can be as high as about 80% of the total weight of the said base.

The compounds of formula I are also appreciated in the flavour industry. Depending on the nature of the products in which they are incorporated, the said compounds can improve, enhance or modify various gustative notes such as woody, slightly earthy or balsamic notes, sometimes reminiscent of those of fresh berries. They are particularly appreciated for the preparation of artificial flavours of walnuts, hazelnuts, peanuts or those of citrus fruits like e.g. lemon or grapefruit, or even those of bilberries or cranberries.

Owing to their specific organoleptic properties the said compounds can also be used for flavouring tobacco and tobacco products. For example, they can improve various woody on amber-like notes reminiscent in some instances of the taste of certain oriental tobaccos.

Depending on the nature of the flavoured material or on the effect desired the proportions used can vary within wide limits. They can be of the order of 1 ppm to 1% of the total weight of the flavoured material.

The more interesting effects can be achieved by the use of proportions comprised between about 50 and about 100 ppm of the total weight of the flavoured product.

When the said compounds are used as ingredients for the preparation of artificial flavours, they can be used in proportions comprised between about 0.1 and about 15% of the total weight of the said flavouring composition, the proportions preferably used being of the order of 1 to 10%.

Among the compounds of formula I which can be used according to the invention the following are new compounds: 6,10-dimethyl-bicyclo[4.4.0]dec-10-en-3-one, cis-6,10-dimethyl-bicyclo[4.4.0]dec-1-en-3-one, cis- and trans-6,10-dimethyl-bicyclo[4.4.0]dec-1-en-3-ol, 6,10-dimethyl-3-acetoxy-bicyclo[4.4.0]dec-1-ene, trans-6,10-dimethyl-trans-bicyclo[4.4.0]decan-3-one-, cis- and trans-6,10-dimethyl-cis-bicyclo[4.4.0]decan-3-one, cis- and trans-6,10-dimethyl-cis-bicyclo[4.4.0]decan-3-one, trans-6,10-dimethyl-trans-bicyclo[4.4.0]decan-3-ol, cis- and trans-6,10-dimethyl-cis-bicyclo[4.4.0]decan-3-ol, cis- and trans-6,10-dimethyl-3-acetoxy-cis and trans-bicyclo[4.4.0]-decane.

Owing to the presence of various substituents in positions 1, 3, 6 and 10 of the decaline skeleton, the formula I can represent several isomeric forms of the given compound. In the course of the present specification the said formula describes either a bicyclic compound wherein the hydrogen atom in position 1 can have a cis- or a trans-configuration relative to the methyl group in position 6, or a compound wherein the alkyl substituent in position 10, can possess a cis- or trans-configuration relative to the methyl group in position 6. Moreover, the said compounds of formula I can also possess a hydroxyl or an O-acyl group in an axial or an equatorial configuration. Therefore the said formula represents either an individual stereoisomer or any possible arrangement of the said stereoisomeric forms. Finally owing to the presence of chirality centres in positions 1, 3, 6 and 10 of the bicyclic skeleton the formula I can also represent a racemic or an optically active compound.

According to the invention the compounds of formula I ca be used in a pure isomeric form. However, in some instances, owing to the fact that the gustative or olfactive effect of the given mixture is often similar to that of one of the pure stereoisomeric constituents, for practical and economical reasons, mixtures of stereoisomers as directly obtained by the process of the invention can also be used.

Equally, β6,10-dimethyl-bicyclo[4.4.0]dec-10-en-α3-ol is a new compound. Although the epimeric compound having the hydroxyl group in an equatoral configuration, i.e. β6,10-dimethyl-bicyclo[4.4.0]dec-10-en-β3-ol is practically tasteless and odourless, we have surprisingly found that the epimeric unsaturated alcohol having the hydroxyl group in the axial configuration possesses more pronounced organoleptic properties. The olfactive character of the said alcohol presents a very rounded and tenacious woody note reminiscent of that of patchouli.

The said compound can be obtained by reducing 6,10-dimethyl-bicyclo[4.4.0.]dec-10-en-3-one by means of the reducing agents conventionally used to convert a ketone into the corresponding secondary alcohol. Suitable reducing agents include alkali metal hydrides or aluminiumhydrides. The subsequent separation of the thus obtained reduction mixture by usual chromatography techniques yields the desired compound.

The nomenclature followed for this specific compound was used to better define the two epimeric alcohols: thus β6,10-dimethyl-bicyclo[4.4.0]dec-10-en-α3-ol defines a bicyclic alcohol of formula I wherein the hydroxyl group possesses a trans-configuration relative to the methyl group in position 6.

Known compounds of formula I are described hereinafter:

a. (±) trans-6,10-dimethyl-bicyclo[4.4.0]dec-1-en-3-one:

obtained from 2,6-dimethyl-cyclohexanone and 2,4-dichloro-but-2-ene according to a method described in J. Org. Chem. 34, 3642 (1969) m.p. 28°–29° IR(neat): 1675, 1615, 1460, 1275, 1240, 873 cm$^{-1}$ NMR (CCl$_4$): 1.06 (3H, d, J=6 cps); 1.25 (3H, s); 5.61 (1H, d, J=6 cps) δ ppm MS: M$^+$ = 178; m/e: 136, 135, 122, 121;

b. β6,10-dimethyl-bicyclo[4.4.0]dec-10-en-β3-ol:

prepared by reducing 6,10-dimethyl-3-acetoxy-bicyclo[4.4.0]deca-2,10-diene according to a method described in J. Org. Chem. 31, 2933 (1966).

B.p. 93°–98° C/0.3 Torr. IR (neat): 3330, 1450, 1370, 1060, 1050, 1020 cm$^{-1}$ NMR (CCl$_4$): 1.07 (3H, s); 1.63 (3H, s); 2.75 (1H, m); 4.15 (1H, broad s) δ ppm MS: M$^+$ = 180; m/e 147, 110, 109, 91;

c. cis-6,10-dimethyl-trans-bicyclo[4.4.0]decan-3-ol:

obtained by reducing 6,10-dimethyl-bicyclo[4.4.0]-dec-10-en-3-ol according to a method described in the above cited reference. B.p. 95° C/0.3 Torr. IR (neat): 3330, 1055, 1032 cm$^{-1}$ NMR (CCl$_4$): 0.89 (3H, s); 0.91 (3H, d, J=not computed); 4.10 (1H, m); 4.70 (1H, broad s) δ ppm MS: M$^+$ = (1); m/e 164, 149, 109, 55, 41; and d. (±) cis-6,10-dimethyl-trans-bicyclo[4.4.0]decan-3-one:

prepared by oxidizing the corresondng racemic alcohol according to a method described in the reference cited under letter (b). B.p. 95°–100° C/0.3 Torr. IR (neat): 1715, 1460, 1387, 1235, 940 cm$^{-1}$ NMR (CCl$_4$): 0.93 (3H, d, J=7 cps); 1.13 (3H, s) δ ppm MS: M$^+$ = 180; m/e: 123, 109, 55, 41.

It has to be pointed out that in the above cited references to the literature the use of the said compounds as perfuming and/or flavouring ingredients has never been recognized.

As indicated above some of the compounds of formula I can be prepared by oxidizing compounds of formula II. The said process may formally be visualized as an oxidative splitting of the exocyclic double bond of the said compounds of formula II.

Such a splitting can be effected either according to the conventional methods used to split a carbon-carbon double bond [see e.g. L. F. Fieser and M. Fieser, "Reagents for Organic Chemistry," Vol I, p 773, John Wiley and Sons, New York, 1967], or by means of an alkali metal metaperiodate in the presence of a catalytic amount of osmium tetraoxyde [see e.g. op. cit., p. 812], or by means of a metal oxide such as CrO₃ or of an oxidized metal derivative such as an alkali metal chromate or permanganate in the presence of a strong mineral acid.

The splitting of the said exocyclic double bond can also be achieved by treating the compound of formula II with a peracid, hydrolizing the thus obtained epoxyde and subsequently oxydizing the obtained diol. Suitable organic peracids include performic, peracetic, trifluoroperacetic, perphthalic or m-chloroperbenzoic acid. The said peracid preferably reacts with the higher substituted double bond [see Organic Reactions 7, 378 (1953), J. Wiley and Sons, New York] i.e. the exocyclic double bond of the compound of formula II. The subsequent hydrolysis can be carried out in an acidic medium, e.g. in the presence of a strong mineral acid such as H₂SO₄ or HCl. The oxidation of the thus obtained diol may be effected by means of a strong oxidizing agent, e.g. lead tetraacetate or periodic acid [see e.g. L. F. Fieser and M. Fieser, "Reagents for Organic Chemistry," vol. I, p. 546 and 816, J. Wiley and Sons, New York, 1967].

According to another embodiment of the process of the invention the oxidative splitting of the exocyclic double bond of the compound of formula II can also be effected by means of singlet oxygen and subsequent treatment of the obtained oxidation mixture with an acidic reagent. Singlet oxygen can be generated by dye-sensitized photooxygenation. Dyes such as porphyrines, methylene blue, eosin, chlorophyl, Rose Bengal or xanthene are conveniently used [see e.g Liebigs Ann. Chem. 674, 93 (1964); Angew. Chem. 69, 579 (1957)]. Said photooxygenation can be carried out at a temperature near to or lower than 0° C, and in the presence of an aqueous or organic medium. Suitable solvents include water, an aqueous organic solvent, an aromatic or aliphatic hydrocarbon such as e.g. benzene, toluene or n-hexane, an alcohol, e.g. methyl or ethyl alcohol, an ether such as e.g. dioxan or tetrahydrofuran, or a mixture of at least two of the above mentioned solvents. Equally as acidic reagents Lewis acids can be conveniently used. For instance, a metal halide such as AlCl₃, ZnCl₂, SnCl₄ or FeCl₃ can be employed. BF₃ is however preferred.

In accordance with the process of the invention it is now possible to convert cis- or trans-6,10-dimethyl-3-isopropylidene-trans-bicyclo[4.4.0]decane into cis- or trans-6,10-dimethyl-trans-bicyclo[4.4.0]decan-3-one. The bicyclic hydrocarbons used as starting materials in the above process can be obtained by reducing a mixture of α- and β-eudesmol and subsequently dehydrating the thus obtained bicyclic alcohols. The preparation of the above mentioned ketone as well as that of the starting material can be illustrated by the following reaction scheme:

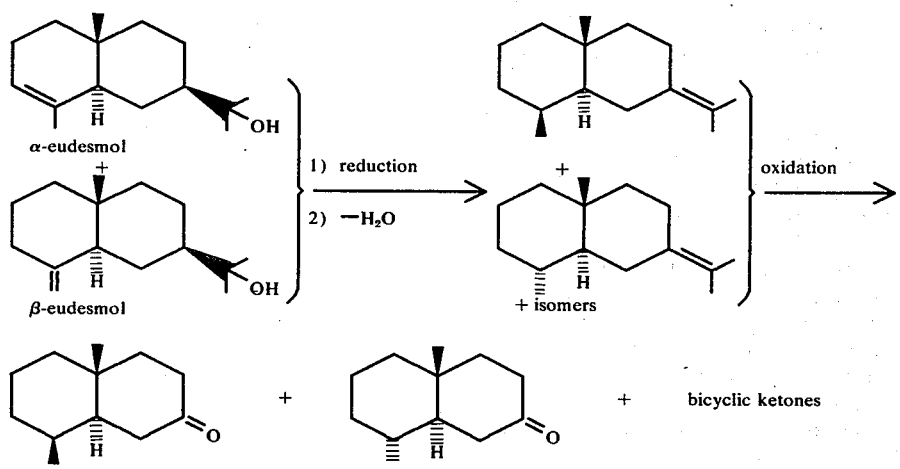

Starting from a naturally occurring mixture of α- and β-eudesmol there is obtained a mixture of the desired bicyclic ketones together with the bicyclic ketones containing 14 carbon atoms. Finally, the desired compounds can be obtained in a pure state after separation of the above mixture by means of the conventional techniques such as e.g. column or preparative vapour phase chromatography.

The compounds of formula which possess a cyclic double bond can be used as starting materials for the preparation of compounds having a saturated bicyclic skeleton. The said starting materials can be reduced according to the usual techniques, for example by catalytic hydrogenation of trans-6,10-dimethyl-bicyclo[4.4.0]dec-1-en-3-one yields trans-6,10-dimethyl-cis or trans-bicyclo[4.4.0]decan-3-one. Moreover, over, the compounds of formula I wherein the symbols X are taken together and represent an oxygen atom can be converted into the corresponding hydroxy-derivatives. By esterifying the thus obtained alcohols it is also possible to obtain the corresponding esters, e.g. the formates, the acetates, propionates or butyrates. When combining both reduction and esterification, it is thus possible to obtain the said esters in a single process from the corresponding saturated or unsaturated bicyclic ketones. By reducing trans-6,10-dimethyl-trans-bicyclo[4.4.0]decan-3-one by catalytic hydrogenation in the presence of acetic acid and a catalytic amount of a strong mineral acid such as sulphuric or perchloric acid, trans-6,10-dimethyl-3-acetoxy-trans-bicyclo[4.4.0]decane is thus obtained. Finally, the compounds of formula I wherein one of the symbols X represents a hydroxyl group and the other is a hydrogen atom can be oxidized to afford the corresponding ketones. Trans-6,10-dimethyl-trans-bicyclo[4.4.0]decan-3-one is thus obtained by oxidation of trans-6,10-dimethyl-trans-bicyclo[4.4.0]decan-3-ol by means of a reactant usually known in the art to convert a secondary alcohol into the corresponding ketone. In the same way 6,10-dimethyl-bicyclo[4.4.0]dec-10-en3-one is prepared from 6,10-dimethyl-bicyclo[4.4.0]dec-10-en3-ol.

As indicated above some of the compounds of formula I can be prepared by isomerizing the cyclic double bond of compounds of formula I wherein the symbols X are taken together and represent an oxygen atom and wherein one of the symbols R and R' represent a lower alkyl group and the other is a hydrogen atom when both the indexes m and n are identical and equal to 1 and p is zero.

The said isomerization can be carried out in the presence of a solvent such as e.g. dimethyl sulfoxide, ter-butanol, tetrahydrofuran or liquid ammonia and in the presence of a strong base such as e.g. potassium ter-butoxide, sodium hydride, or potassium or sodium amide, and subsequent treatment of the thus formed enolate with an acidic reagent such as e.g. acetic or boric acid or sodium dihydrogenophosphate [see Tetrahedron Letters 1962, 669]. Thus according to a particular embodiment of the process of the invention trans-6,10-dimethyl-bicyclo[4.4.0]dec-1-en-3-one can be converted into 6,10-dimethyl-bicyclo[4.4.0]dec-10-en-3-one.

The invention is illustrated in a more detailed manner by the following examples wherein the temperatures are given in degrees centigrade.

| | |
|---|---:|
| α-Phenylethyl acetate | 30 |
| Undecenal 10 %* | 100 |
| α-Methylundecenal 10 %* | 20 |
| Coumarin | 60 |
| Vanillin | 5 |
| Musk ketone | 55 |
| Cyclopentadecanone 10 %* | 30 |
| α-Isomethylionone | 60 |
| Absolute oak moss | 20 |
| Absolute labdanum | 10 |
| Synthetic galbanum | 10 |
| Synthetic castoreum | 20 |
| Methyl 2-pentyl-3-oxo-cyclopentyl-acetate | 50 |
| Benzyl acetate | 100 |
| Indol 10 %* | 10 |
| Hexylcinnamic aldehyde | 50 |
| Synthetic rose | 50 |
| Patchouli | 20 |
| Synthetic bergamot | 200 |
| Total | 900 |

*in diethyl phthalate

By adding to 90 g of the above composition 10 g of a 10% solution of trans-6,10-dimethyl-bicyclo[4.4.0]-dec-1-en-3-one, 6,1.-dimethyl-bicyclo[4.4.0]dec-10-en-3-one or 6,10-dimethyl-bicyclo[4.4.0]dec-10-en-3-ol, in diethyl phthalate, there was obtained a new perfume composition possessing a very elegant and original woody character, having moreover a very natural richness.

By adding in the same proportions 6,10-dimethyl-cis- or trans-bicyclo[4.4.0]decan-3-one or trans-6,10-dimethyl-3-acetoxy-trans-bicyclo[4.4.0]decane to the above base there was obtained a perfume composition possessing a very rich woody and amber-like note.

By adding in the same proportions either trans-6,10-dimethyl-3-acetoxy-bicyclo[4.4.0]dec-1-ene, or 6,10-dimethyl-3-acetoxy-bicyclo[4.4.0]dec-10-ene or one of the corresponding saturated or unsaturated alcohols to the above base, there was obtained a perfume composition possessing a new and agreable woody, sometimes slightly balsamic character.

In most instances it was observed that the said woody note was very tenacious.

EXAMPLE 2

A base perfume composition for a masculine Eau de Cologne was prepared by admixing the following ingredients (parts by weight):

| | |
|---|---:|
| Sage oil | 20 |
| Lavender oil | 150 |
| Synthetic bergamot | 200 |
| Lemon oil | 140 |
| Sweet orange oil | 40 |
| Synthetic galbanum 10 %* | 20 |
| Muscone 10 %* | 50 |
| Methyl 2-pentyl-3-oxo-cyclopentyl-acetate | 10 |
| 1,1-Dimethyl-6-ter-butyl-4-acetylindane | 10 |
| α-Isomethylionone | 50 |
| Synthetic ylang | 80 |
| Synthetic jasmine | 25 |
| Synthetic geranium | 50 |
| Synthetic neroli | 100 |
| Coriander oil | 5 |
| Total | 950 |

*in diethyl phthalate

By adding to 95 g of the above base composition 5 g of a 10% solution of trans-6,10-dimethyl-bicyclo[4.4.0]dec-1-en-3-one, 6,10-dimethyl-bicyclo[4.4.0]dec-10-en-3-one, 6,10-dimethyl-bicyclo[4.4.0]dec-10-en-3-ol or trans-6,10-dimethyl-cis or trans-bicyclo[4.4.0]decan-3-one in diethyl phthalate, there was obtained a perfume composition possessing a novel and very distinct and tenacious woody odour.

The addition, in the same proportions, of trans-6,10-dimethyl-3-acetoxy-bicyclo[4.4.0]dec-1-ene, 6,10-dimethyl-3-acetoxy-bicyclo[4.4.0]dec-10-ene or trans-6,10-dimethyl-3-acetoxy-trans-bicyclo[4.4.0]decane confers to the above base a novel and particularly agreable woody and slightly balsamic note reminiscent of that of cedar wood.

By adding, in the same proportions, one of the corresponding saturated or unsaturated alcohols to the above base, there was obtained a new perfume composition possessing an agreable, tenacious and slightly green woody odour.

EXAMPLE 3

A base flavouring composition having a taste and an aroma similar to those of walnut was prepared by admixing the following ingredients (parts by weight):

| | |
|---|---:|
| Methyl-cyclopentenolone | 50 |
| Furfuryl alcohol | 50 |
| Furfural | 10 |
| Diacetyl | 5 |
| Acetyl-methylcarbinol | 30 |
| Benzyl alcohol | 100 |
| Propylene glycol | 755 |
| Total | 1000 |

Two flavouring compositions were then prepared as indicated below (parts by weight):

| | A (test) | B (control) |
|---|---:|---:|
| Base composition trans-6,10-Dimethyl-bicyclo | 100 | 100 |

-continued

|  | A (test) | B (control) |
|---|---|---|
| [4.4.0]dec-1-en-3-one | 100 | — |
| Propylene glycol | 800 | 900 |
| Total | 1000 | 1000 |

Both mixtures A and B were then used for the preparation of the following foodstuffs, in the proportions of 100 g of flavouring composition per 100 kg of foodstuff. Ice-cream: An ice-cream mixture was prepared from 1 litre of milk, 5 egg yolks and 250 g of sugar in the following manner: the milk was heated, the sugar and the egg yolks were mixed and the hot milk was added to the mixture while stirring. Stirring was continued until the mass thickened, and the flavour was added. The mixture was then frozen in the usual manner. Pudding: A mixture of 60 g of sugar and 3 g of pectine was added to 500 ml of hot milk, while stirring. The mixture was brought to the boil for a few seconds, the flavour was added and the mixture allowed to cool.

The foodstuffs prepared as described above were then tasted by a panel of flavour experts who declared that the "test" foodstuffs possessed a more pronounced and slightly woody and nutty taste as compared with the "control" foodstuffs.

By substituting, in the above composition, trans-6,10-dimethyl-bicyclo[4.4.0]dec-1-en-3-one by the corresponding saturated ketone or by one of the corresponding saturated or unsaturated alcohols or esters, a similar effect was observed. In this latter case, however, it was necessary to use higher proportions.

EXAMPLE 4

A commercial bilberries jam was flavoured with a 10% ethanolic solution of trans-6,10-dimethyl-bicyclo[4.4.0]dec-1-en-3-one, in the proportions of 15 ml of said ethanolic solution per 100 kg of flavoured material. The thus flavoured foodstuff was then compared by a panel of flavour experts with an unflavoured jam containing ethyl alcohol in the above given proportions. It was declared that the flavoured jam possessed a woody, slightly balsamic taste reminiscent of that of fresh bilberries.

An analogous effect was observed by adding, in the same proportion, the corresponding saturated ketone or one of the corresponding saturated or unsaturated alcohols or esters to the above foodstuff. The woody taste had in this case a more pronounced green character.

EXAMPLE 5

To 1 litre of an acidulous sugar syrup (prepared by diluting 650 g of sucrose and 10 ml of a 50% aqueous solution of citric acid in 1000 ml of water), flavoured with lemon or grapefruit oil in the proportion of 30 g of the said oil per 100 l of syrup, there was added 1 ml of a 1% ethanolic solution of trans-6,10-dimethyl-bicyclo[4.4.0]dec-1-en-3-one. The thus flavoured beverage was then compared with an unflavoured syrup by a panel of flavour experts. These latter declared that the flavoured syrup as compared with the unflavoured one, possessed an agreable and more marked fruity taste with a slightly woody character.

By substituting, in the above beverage, trans-6,10-dimethyl-bicyclo[4.4.0]dec-1-en-3-one by the corresponding saturated ketone or by one of the corresponding saturated or unsaturated alcohols or esters, a similar effect was observed. In this latter case it was however necessary to use higher proportions.

EXAMPLE 6

.7 g of a 1% ethanolic solution of trans-6,10-dimethyl-bicyclo[4.4.0]dec-1-en-3-one were sprayed onto 100 g of an "american blend" tobacco mixture. The tobacco thus flavoured was used for the manufacture of "test" cigarettes, the smoke of which was then subjected to organoleptic evaluation by comparison with unflavoured "control" cigarettes. The tobacco used to prepare the "control" cigarettes was preliminary treated with a corresponding amount of ethyl alcohol.

A panel of flavour experts defined the taste of the smoke of the "test" cigarettes as being more rounded than that of the "control" cigarettes, the said smoke possessing moreover a more marked woody character.

By following the same flavouring procedure, the panel of experts declared that the smoke of "test" cigarettes flavoured by 6,10-dimethyl-bicyclo[4.4.0]-dec-1-en-3-ol possessed a more intense woody taste reminiscent of that of cedar wood and, in some instances, the taste of certain oriental tobaccos.

EXAMPLE 7

(+)
cis-6,10-Dimethyl-trans-bicyclo[4.4.0]decan-3-one
and (−)
trans-6,10-dimethyl-trans-bicyclo[4.4.0]decan-3-one 600 mg (2.36 mM) of osmium tetroxide have been added at room temperature and under stirring to 1.56 g (7.55 mM) of a mixture of cis- and trans-6,10-dimethyl-3-isopropylidene-trans-bicyclo[4.4.0]decane and cis- and trans-6,10-dimethyl-3-isopropenyl-trans-bicyclo[4.4.0]decane (which has been prepared in accordance with a process as hereinbelow described) dissolved in a mixture of 130 ml of acetone, 20 ml of water and 3 ml of acetic acid.

15 minutes after the end of the addition, there are added 5.0 g (23.4 mM) of sodium metaperiodate while stirring. After having been left overnight at room temperature, the reaction mixture has been diluted with water and extracted with 3 portions of 5 ml each of ether. By the usual treatments of washing, drying and evaporation the ethereal organic phase gave 2.40 g of residue, which was then submitted to a column chromatography on silicagel 0.05–0.2 mm. An elution with a mixture of n-hexane/$CH_2Cl_2$ (3:1) gave a first fraction of 800 mg (ca. 51%) of a 2:3 mixture of the bicyclic ketones of formula

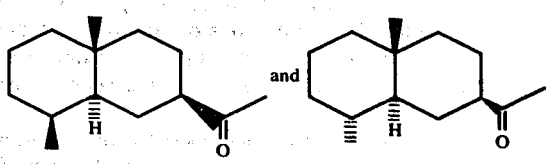

followed by a second fraction of 275 mg (ca. 20%) of a 2:3 mixture of the desired ketones. These latter have been finally separated one from the other by preparative vapour phase chromatography. (+) cis-6,10-dimethyl-trans-bicyclo[4.4.0]decan-3-one:
$[\alpha]_D^{20} = +3.7°$ (0.65% in $CHCl_3$)
IR (neat) : 1715, 1460, 1387, 1235, 940 $cm^{-1}$ NMR (CCl$_4$) : 0.93 (3H,d,J=7 cps); 1.13 (3H,s) δ ppm MS: M$^+$ = 180; m/e = 123, 109, 55, 41. (−) trans-6,10-dimethyl-trans-bicyclo[4.4.0]decan-3-one :

[α]$_D^{20}$ = −43.9 (1.0% in CHCl$_3$)

IR (neat) : 1715, 1460, 1387, 1235, 940 cm$^{-1}$

NMR (CCl$_4$) : 0.83 (3H,d,J=5 cps); 1.05 (3H,s) δ ppm

MS : M$^+$ = 180; m/e = 123, 109, 55, 41.

The mixture of the isomeric bicyclic hydrocarbons, used as starting materials in the hereinabove preparation, has been synthesized as follows :

5.20 g (23.4 mM) of a 9:7 mixture of α- and β-eudesmol [isolated from eucalyptus oil : [α]$_D^{20}$ = +33.7° (2.6% in CHCl$_3$)] dissolved in 70 ml ethanol, have been hydrogenated at room temperature in the presence of 200 mg of palladium on charcoal (10%). After filtration and evaporation of the clear filtrate, there are obtained 5.2 g of a raw mixture of the bicyclic isomeric saturated alcohols. 2.0 g (8.90 mM) of the above mixture, dissolved in 6 ml of anhydrous pyridine, have been added dropwise to a cooled (0°) solution of 16 ml of phosphorous oxychloride in 60 ml of anhydrous pyridine. After having been stirred at room temperature during 3 hours, the reaction mixture was poured onto crushed ice and extracted with ether. The usual treatments of washing with water and a 10% aqueous solution of HCl followed by neutralisation with a saturated aqueous solution of NaHCO$_3$, drying over MgSO$_4$ and evaporation, gave 1.65 g (90% yield) of a mixture of cis- and trans-6,10-dimethyl-3-isopropenyl-trans-bicyclo[4.4.0]decane and cis- and trans-6,10-dimethyl-3-isopropylidene-trans-bicyclo[4.4.0]decane in the proportions of 49:30:13:8, respectively.

EXAMPLE 8 (+)

cis-6,10-dimethyl-trans-bicyclo[4.4.0]decan-3-one and (−) trans-6,10-dimethyl-bicyclo[4.4.0]decan-3-one 4.15 g (ca. 20 mM) of a mixture of cis- and trans-6,10-dimethyl-3-isopropylidene-trans-bicyclo[4.4.0]-decane and of cis- and trans-6,10-dimethyl-3-isopropenyl-trans-bicyclo[4.4.0]decane, obtained according to Example 7, dissolved in 50 ml of a mixture of benzene/methanol (50:50), have been irradiated during 90 min at 20° in the presence of gaseous oxygen and 30 mg of Rose Bengal and 30 mg of hydroquinone. A mercury vapour lamp type Philips HPK of 125 W was used at this end. After evaporation of the volatile fractions under reduced pressure, the thus obtained residue was dissolved in 50 ml of ether - 6 ml of a 48% solution of BF$_3$ in ether were then added to the obtained ethereal solution and the mixture kept at room temperature during 1 hr. The reaction mixture was treated with water and extracted with ether, and the combined organic extracts worked up as usual. There were thus obtained 3.6 g of a raw material which, upon the same procedure as that followed in Example 7, afforded the desired bicyclic ketones.

EXAMPLE 9 trans-6,10-Dimethyl-trans-bicyclo[4.4.0]decan-3-one

A solution of 600 mg (3.37 mM) of trans-6,10-dimethyl-bicyclo[4.4.0]-dec-1-en-3-one in 10 ml of anhydrous ether, have been added in 10 min. to a solution of 100 mg (14.3 m-atom-g) of Li in 80 ml of liquid ammonia.

The reaction mixture has been heated to reflux during 4 hr, 1.5 g of NH$_4$Cl have been added thereto and the excess ammonia taken off. After addition of a 1:1 mixture of ether and water, 550 mg (ca. 90% yield) of raw material was collected by evaporation of the organic phase. By purification by column chromatography on silicagel (eluant:n-hexane/CH$_2$Cl$_2$ 3:1) and subsequent fractional distillation in a bulb tube under reduced pressure (0.01 Torr) there are obtained 180 mg (yield 30%) of the desired product, which was identical in all respects to the product obtained according to the procedure described in Example 7.

EXAMPLE 10 trans-6,10-Dimethyl-trans-bicyclo[4.4.0]decan-3-one 3.4 g (34 mM) of CrO$_3$ have been added at room temperature to a solution of 5.7 ml of pyridine in 75 ml of CH$_2$Cl$_2$. A solution of 1.0 g (5.48 mM) of trans-6,10-dimethyl-trans-bicyclo[4.4.0]decan-3-ol in 5 ml CH$_2$Cl$_2$ was slowly added thereto under stirring and the reaction mixture kept at room temperature during 30 min, whereupon it was poured onto crushed ice and extracted with n-pentane. The organic phase was washed with a 2N NaOH solution, followed by a 2N HCl aqueous solution and a saturated NaCl aqueous solution. The usual treatment of drying over MgSO$_4$, evaporation to dryness and purification of the raw residue thus obtained (0.85 g), by column chromatography on silicagel (eluant: a 8:2 mixture of hexane and CH$_2$Cl$_2$) gave 750 mg (76% yield) of the desired product, which was identical in all respects to that obtained in accordance with the procedure described in Example 7.

EXAMPLE 11 trans-6,10-Dimethyl-bicyclo[4.4.0]dec-1-en-3-ol

A solution of 1.0 g (5.6 mM) of trans-6,10-dimethyl-bicyclo[4.4.0]dec-1-en-3-one in 10 ml of anhydrous ether was added dropwise at room temperature to a suspension of 75 mg (2-m-atom-g) of LiAlH$_4$ in 50 ml of anhydrous ether. The reaction mixture was then heated to reflux during 2 hr, treated with a 1:1 mixture of methanol and water, filtered and the organic phase finally separated.

By evaporation to dryness there were thus obtained 920 mg (ca. 90%) of raw material, which, upon purification by column chromatography on silicagel (eluant : CH$_2$Cl$_2$), gave a product which was then subjected to fractional distillation in a bulb apparatus under reduced pressure (0.05 Torr) to give 400 mg (40% yield) of the desired product. IR (neat): 3330, 1650, 1455, 1372, 1050, 989 cm$^{-1}$ NMR (CDCl$_3$): 1.0 (3H,d,J=6.5 cps); 1.1 (3H,s); 3.78 (1H, broad s); 4.1 (1H,m); 5.25 (1H,m,J<2 cps) δ ppm. MS : M$^+$ = 180 (22); m/e = 147 (60), 110 (87), 109 (100), 91 (84).

EXAMPLE 12 trans-6,10-Dimethyl-trans-bicyclo[4.4.0]decan-3-ol

A solution of 2.0 g (11.2 mM) of trans-6,10-dimethyl-bicyclo[4.4.0]dec-1-en-3-one in 50 ml of anhydrous tetrahydrofuran was added to a mixture of 50 ml of ter-butanol and 200 ml of liquid ammonia. To this mixture cooled at −37° there were added by small portions and under stirring 2.2 g (314 m-atom-g) of lithium, whereupon the mixture was kept under stirring until discoloration (ca. 5 hr). By evaporation of the excess ammonia, there was obtained a residue which was then taken up by a 1:1 mixture of ether and water.

The organic phase gave by the usual treatments of washing and drying 2.0 g (ca. 98% yield) of a raw material which was then purified by column chromatography on silica gel (eluant : $CH_2Cl_2$/methanol, 50:50) and finally distilled under vacuum in a bulb apparatus (0.01 Torr).

1.2 g (ca. 59% yield) of the desired product were thus obtained. The gas chromatographic analysis revealed that the product consisted of one stereoisomer only. IR (neat) : 3340, 1455, 1170, 975, 610 cm$^{-1}$ NMR ($CCL_4$) : 0.82 (3H,d,J=5 cps); 0.85 (3H,s); 3.33 (1H,m); 3.91 (1H,s), δ ppm MS: M$^+$ = 182; m/e = 149, 109, 55, 41.

EXAMPLE 13 trans-6,10-Dimethyl-bicyclo[4.4.0]decan-3-ol

A solution of 500 mg (2.78 mM) of trans-6,10-dimethyl-trans-bicyclo[4.4.0]decan-3-one in a mixture of 30 ml of glacial acetic acid and 1 ml of a 70% aqueous solution of $HClO_4$, has been hydrogenated at room temperature in the presence of 120 mg of $PtO_2$. The reaction mixture has then been filtered and taken up by a 1:1 mixture of ether and water. By separation of the organic phase and evaporation to dryness, there were obtained 500 mg of raw material. This latter was taken up by 10 ml of dry ether and added dropwise at room temperature to a suspension of 100 mg of $LiAlH_4$ in 50 ml of dry ether. After having been left during 3 hr at room temperature the reaction mixture was treated with a 1:1 mixture of methanol and water, filtered and the clear filtrate finally extracted with ether. The usual treatments of washing, drying and evaporation gave 430 mg (yield : 85%) of a mixture of the epimeric alcohols A and B, whose separation was realized by preparative vapour phase chromatography. A : this product was identical to that of Example 12; B : M.p. 124°–125° IR ($CCl_4$) : 3630, 1455, 1055, 910 cm$^{-1}$ NMR ($CDCl_3$) : ca. 0.85 (3H,s et 3H,d partially masked); 4.04 (1H,m); 4.71 (1H,s) δ ppm MS: M$^+$ = 182 (<1); m/e : 164, 149, 109, 55, 41.

EXAMPLE 14 trans-6,10-Dimethyl-3-acetoxy-bicyclo[4.4.0]dec-1-ene 450 mg (2.5 mM) of trans-6,10-dimethyl-bicyclo[4.4.0]dec-1-en-3-ol have been reacted at 20° overnight with a mixture of 5 ml of pyridine and 2 ml of acetic anhydride. The reaction mixture was then poured onto ice and extracted with water. The organic phase was washed with a 2N aqueous solution of NaHCO$_3$, a 10% solution of HCl and a saturated aqueous solution of NaCl, and finally dried over MgSO$_4$. By evaporation to dryness 500 mg of raw material were obtained. Subsequent purification by column chromatography on 30 g of silica gel yielded on elution with CH$_2$Cl$_2$ a fraction which upon distillation under reduced pressure (0.05 Torr) gave 300 mg (ca. 55% yield) of the desired product. IR (neat) : 1735, 1650, 1460, 1375, 1245 cm$^{-1}$ NMR ($CCl_4$) : 0.99 (3H,d,J=6.5 cps); 1.1 (3H,s); 2.0 (3H,s); 5.2 (2H,m) δ ppm MS : M$^+$ = 222 (4); m/e = 162 (57), 147 (100), 105 (60), 91 (86).

EXAMPLE 15

6,10-Dimethyl-3-acetoxy-bicyclo[4.4.0]dec-10-ene 450 mg (2.5 mM) of 6,10-dimethyl-bicyclo[4.4.0]dec-10-en-3-ol were acetylated according to the same procedure as given in Example 14. By purification of the raw material by fractional distillation under vacuum (0.05 Torr) in a bulb apparatus, there were obtained 400 mg (ca. 75% yield) of the desired product. IR ($CCl_4$) : 1735, 1475, 1462, 1245, 1035 cm$^{-1}$ NMR ($CCl_4$) : 1.05 (3H,s); 1.61 (3H,s); 1.94 (3H,s); 2.78 (1H,d of d, J$_1$ = 14 cps, J$_2$=4.5 cps); 4.45 (1H,m) δ ppm MS : M$^+$ = 222 (<1); m/e = 162 (76), 147 (100), 91 (26), 43 (35).

EXAMPLE 16 trans-6,10-Dimethyl-3-acetoxy-trans-bicyclo[4.4.0]-decane

A solution of 1.0 g ca. 5.6 mM) of trans-6,10-dimethyl-trans-bicyclo[4.4.0]decan-3-one in 50 ml of glacial acetic acid and 2 ml of a 70% aqueous solution of HClO$_4$, has been subjected to hydrogenation at 20° in the presence of 200 mg of PtO$_2$. After filtration, the reaction mixture has been taken up by a 1:1 mixture of ether and water. By the usual treatments of washing and drying, 1.0 g of raw material was obtained (yield ca. 80%). On distillation of this residue under vacuum (0.05 Torr), there were obtained 810 mg (65% yield) of a mixture of the epimeric esters A and B, which were then separated by preparative vapour phase chromatography. A : IR (neat) : 1735, 1455, 1375, 1360, 1245, 1025 cm$^{-1}$ NMR (CCl$_4$) : 0.85 (3H,d,J=5.5 cps); 0.90 (3H,s); 1.96 (3H,s); 4.60 (1H,m) δ ppm MS : M$^+$ = 224 (<1); m/e = 164 (73), 149 (100), 110 (60), 109 (68), 43 (89). B : IR (neat) : 1735, 1455, 1430, 1375, 1360, 1245, 1220, 1015 cm$^{-1}$ NMR (CCl$_4$) : 0.80 (3H,d,J=5 cps); 0.85 (3H,s); 1.98 (3H,s); 5.01 (1H,m) δ ppm MS : M$^+$ = 224 (<1); m/e = 164 (72), 149 (100), 109 (62), 108 (45), 43 (65).

EXAMPLE 17

6,10-Dimethyl-bicyclo[4.4.0]dec-10-en-3-one

A solution of 2.0 g (11.5 mM) of trans-6,10-dimethyl-bicyclo[4.4.0]dec-1-en-3-one and 12.0 g (ca. 110 mM) of potassium ter-butylate in 75 ml of ter-butanol, has been stirred during 2 hr at room temperature under an inert atmosphere of nitrogen. 400 ml of a 10% aqueous solution of acetic acid were then added thereto and the thus obtained mixture rapidly neutralized with a saturated aqueous solution of NaHCO$_3$. By extraction with ether followed by washing, drying, evaporation and purification by column chromatography on silica-gel (elution with CH$_2$Cl$_2$), there were obtained 1.80 g (90% yield) of the desired product. IR (neat) : 1710, 1600 cm$^{-1}$ NMR (CCl$_4$) : 1.20 (3H,s); 1.58 (3H, large s); 2.27 (2H,t,J=5 cps); 3.10 (2H,m) δ ppm MS : M$^+$ = 178 (57); m/e = 163 (100), 123 (45), 93 (42).

EXAMPLE 18

6,10-Dimethyl-bicyclo[4.4.0]dec-10-en-3-one 2.5 g (ca. 14 mM) of 6,10-dimethyl-bicyclo[4.4.0]-dec-10-en-3-ol have been oxidized by means of a CrO$_3$/pyridine complex according to the same procedure as given in Example 10. By purification by column chromatography, there were obtained 2.1 g (ca. 85%)

of the desired product, which was in all respects identical with that described in Example 17.

EXAMPLE 19 trans-6,10-Dimethyl-cis-bicyclo[4.4.0]decan-3-one

A solution of 2.0 g (ca. 11.5 mM) of trans-6,10-dimethyl-bicyclo[4.4.0]dec-1-en-3-one in 30 ml ethanol and 3 ml of a 10% aqueous solution of HCl has been hydrolysed at room temperature in the presence of 10% Pd on charcoal. Once the reduction was over, the reaction mixture was filtered, concentrated under vacuum and the thus obtained residue purified by column chromatography on silicagel (eluant : $CH_2Cl_2$) to afford 1.6 g (ca. 80% yield) of a mixture comprising 90% of the desired bicyclic ketone and 10% of trans-6,10-dimethyl-trans-bicyclo[4.4.0]decan-3-one (see Example 7). These two isomeric bicyclic ketones may be separated by preparative vapour phase chromatography. IR (neat) : 1710, 1460 $cm^{-1}$ NMR : 0.80 (3H,d,J=6.5 cps); 1.05 (3H,s) δ ppm. MS : $M^+$= 180 (61); m/e = 109 (100), 108 (80), 55 (66), 41 (64).

EXAMPLE 20

β6,10-Dimethyl-bicyclo[4.4.0]dec-10-en-β3-ol
(isomer A) and
β6,10-Dimethyl-bicyclo[4.4.0]dec-10-en-α3-ol
(isomer B)

A solution of 18.0 g (100 mM) of 6,10-dimethyl-bicyclo[4.4.0]dec-10-en-3-one in 150 ml of anhydrous ether, has been subjected to reduction by means of $LiAlH_4$ according to the method described in Example 11.

From the mixture of the isomeric alcohols thus obtained (15.5 g; yield ca. 85%), the pure epimeric isomers were isolated. A : IR (neat) : 3620, 3340, 1060, 1050 $cm^{-1}$ NMR ($CCl_4$) : 1.05 (3H,s); 1.60 (3H,s); 2.76 (1H,d of d,$J_1$=3 cps, $J_2$=13 cps); 3.40 (1H,m); 4.75 (1H, broad s) δ ppm MS : $M^+$ = 180 (18); m/e = 165 (29); 147 (100), 105 (21), 91 (25). B : IR (neat) : 3620, 3580, 1365, 1010 $cm^{-1}$ NMR ($CCl_4$) : 1.05 (3H,s); 1.63 (3H,s); 4.05 (1H,m) δ ppm MS : $M^+$ = 180 (16); m/e = 165 (26), 147 (100), 105 (19), 91 (22).

We claim:
1. A perfume composition comprising at least one bicyclic compound of formula

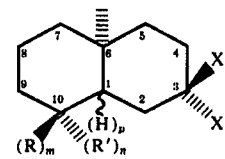

containing a single or a double bond in one of the positions indicated by the dotted lines and wherein the indexes m, n and p represent the integers zero or 1, one of the symbols X represents a hydroxyl or an O-acetyl group and the other represents a hydrogen atom, and wherein the symbol R represents a methyl group when both n and p are identical and equal to zero and m is 1; or one of the symbols R and R' represents a methyl group and the other is a hydrogen atom when both m and and n are identical and equal to 1 and p is zero; or one of the symbols R and $R^1$ represents a methyl group and the other is a hydrogen atom when all indexes m, n and p are equal to 1 and an inert diluent or a carrier.

2. The perfume composition of claim 1 wherein the bicyclic compound is β6,10-Dimethyl-bicyclo[4.4.0]-dec-10-en-α3-yl acetate.

3. The perfume composition of claim 1 wherein the bicyclic compound is trans-6,10-Dimethyl-bicyclo[4.4.0]dec-1-en-3-ol.

4. The perfume composition of claim 1 wherein the bicyclic compound is trans-6,10-Dimethyl-3-acetoxy-bicyclo[4.4.0]dec-1-ene.

5. The perfume composition of claim 1 wherein the bicyclic compound is trans-6,10-Dimethyl-trans-bicyclo[4.4.0]decan-3-ol.

6. The perfume composition of claim 1 wherein the bicyclic compound is trans-6,10-Dimethyl-3-acetoxy-trans-bicyclo[4.4.0]decane.

7. The perfume composition of claim 1 wherein the bicyclic compound is β6,10-Dimethyl-bicyclo[4.4.0]-dec-10-en-α3-ol.

* * * * *

UNITED STATES PATENT AND TRADEMARK OFFICE
CERTIFICATE OF CORRECTION

PATENT NO. : 4,008,184
DATED : February 15, 1977
INVENTOR(S) : Bruno Maurer et al.

It is certified that error appears in the above-identified patent and that said Letters Patent are hereby corrected as shown below:

Column 2, third formula reads 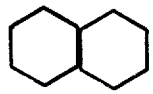, should read 

Column 3, lines 25-6 read "Girard's reagent", should read --Girard's P reagent--

Column 3, line 27 reads "was the", should read --was then--

Column 4, line 20 reads "grup", should read --group--

Column 5, line 6, reads "woody on", should read --woody or--

Column 5, line 57, reads "ca", should read --can--

Column 5, line 66, reads "equatoral", should read --equatorial--

Column 6, line 28, reads "28-29°", should read --28-29°C--

Column 6, line 46, reads "M+=(1)", should read --M+=182(1)--

Column 8, line 47-8, reads "Moreover, over", should read --Moreover,--

Column 9, line 31, should read --Example 1.
A base perfume composition of the Chypre type was prepared by admixing the following ingredients (parts by weight):

UNITED STATES PATENT AND TRADEMARK OFFICE
CERTIFICATE OF CORRECTION

PATENT NO. : 4,008,184 (PAGE 2 of 2)
DATED : February 15, 1977
INVENTOR(S) : Bruno Maurer, et al.

It is certified that error appears in the above-identified patent and that said Letters Patent are hereby corrected as shown below:

Column 9, line 52, reads "6,1.", should read --6,10--

Column 13, line 36, reads "Example 8(+)" and should read
 --Example 8--

Column 13, line 37, reads "cis-6," and should read
 --(+)cis-6,--

Column 18, lines 5-10 reads 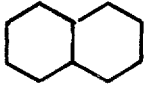 , should read 

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*